United States Patent [19]

Lynch et al.

[11] 4,207,001
[45] Jun. 10, 1980

[54] PARTICLE SIZE ANALYZER

[75] Inventors: Alban J. Lynch; Eugene Gallagher, both of St. Lucia, Australia

[73] Assignee: The University of Queensland, St. Lucia, Australia

[21] Appl. No.: 11,198

[22] Filed: Feb. 12, 1979

Related U.S. Application Data

[63] Continuation of Ser. No. 856,412, Dec. 1, 1977, abandoned, which is a continuation of Ser. No. 689,343, May 24, 1976, abandoned.

[51] Int. Cl.² .................... G01N 15/02; G01N 21/48; G01N 21/26
[52] U.S. Cl. ................................. 356/335; 250/574; 356/340
[58] Field of Search ............... 356/102, 210, 335, 340; 250/574, 575, 578; 235/92 PC

[56] References Cited

U.S. PATENT DOCUMENTS

| | | | |
|---|---|---|---|
| 2,494,441 | 1/1950 | Hillier | 356/102 |
| 2,730,008 | 1/1956 | McGinn | 356/102 |
| 2,891,722 | 6/1959 | Nuttall | 356/102 |
| 3,349,227 | 10/1967 | Martens | 356/102 |
| 3,817,628 | 6/1974 | Adams | 356/210 |
| 3,842,252 | 10/1974 | Jakeman | 356/102 |
| 3,855,455 | 12/1974 | Allinger | 356/102 |
| 3,867,613 | 2/1975 | Schoon | 356/102 |
| 3,892,492 | 7/1975 | Eichenberger | 356/210 |

FOREIGN PATENT DOCUMENTS

| | | | |
|---|---|---|---|
| 671377 | 5/1952 | United Kingdom | 356/102 |
| 758083 | 9/1956 | United Kingdom | 356/102 |
| 808020 | 1/1959 | United Kingdom | 356/335 |
| 974635 | 11/1964 | United Kingdom | 356/335 |
| 1259038 | 1/1972 | United Kingdom | 356/102 |
| 1267774 | 3/1972 | United Kingdom | 356/102 |
| 1370431 | 10/1974 | United Kingdom | 356/102 |
| 1376135 | 12/1974 | United Kingdom | 356/335 |

*Primary Examiner*—Samuel W. Engle
*Assistant Examiner*—Donald P. Walsh
*Attorney, Agent, or Firm*—Parmelee, Johnson, Bollinger & Bramblett

[57] ABSTRACT

A particle size analyzer having an optical assembly with a light source and a lens producing by reflected light an image of a field of particles carried on a moving conveyor. The image is cast upon two photo-transducers which produce substantially identical signals relatively displaced in time by an amount inversely proportional to the rate of conveyor movement. These two transducer signals are fed to discriminator means to develop respective sets of pulse signals identifying predetermined transition characteristics in the light transmitted to the transducers. These two sets of pulse signals are used to develop a control signal for adjusting the frequency of a clock-pulse generator such that a given number of clock pulses represents a corresponding distance moved by the conveyor, irrespective of its speed. One of the sets of pulse signals is used to gate the generated clock pulses to a counter and accumulator system which provides output signals representing certain particle size parameters.

20 Claims, 3 Drawing Figures

PARTICLE SIZE ANALYZER

This is a continuation of application Ser. No. 856,412, filed Dec. 1, 1977, which in turn is a continuation of Ser. No. 689,343, filed May 24, 1976, now both abandoned.

BACKGROUND OF THE INVENTION

This invention relates to apparatus and techniques for the direct measurement of the size distribution of particles in a field of particles. More particularly, this invention relates to measurements of size parameters of mineral particles in mineral processing or quarry plants in which size distribution information is needed for quality or process control.

Data on size distribution is conventionally obtained by mechanical removal of a sample, passing the sample through screens of decreasing aperture, and weighing the material on each screen. Such an operation may be applied to moving material as for example on a conveyor belt, or static material in a stockpile. The present invention is particularly applicable to a field of physically moving particles. The mechanical sampling and sieving system has the disadvantage of being costly and not being substantially instantaneous, although the results obtained give a reproducible measurement of the weight of particles in each size range.

It has also been proposed to image a stationary surface by transmitted light, such as a microscope slide or a polished mineral surface, and scan the image by a raster scan with processing of the resultant signal. Such a system is complex and not suitable for macroscopic moving particle fields.

BRIEF SUMMARY OF THE INVENTION

In one embodiment of the invention, a particle size analyzer for a moving field of particles comprises: an optical assembly with a light source and a lens producing an image of said field by reflected light such that each edge of adjacent particles and each boundary between superimposed or overlapping particles are shadowed; at least one fixed phototransducer traversed by the moving image and producing an electrical signal from which each said edge and boundary is detectable; signal analyzer means fed by said signals to derive size parameters of said particles from the spacing of said edges and boundaries; and output means to transmit said parameters.

The apparatus may also include automatic compensation means to make the measurement of spacing between the gaps and boundaries independent of the velocity of movement of the field. Additionally, indicator means may provide a digital or analog display showing the relative proportion of particles within each of a series of size ranges.

BRIEF DESCRIPTION OF THE DRAWINGS

The accompanying drawings illustrate a particular embodiment of the invention as applied to mineral particles moving on a conveyor belt.

DETAILED DESCRIPTION OF THE PREFERRED EMBODIMENT

Figure 1:
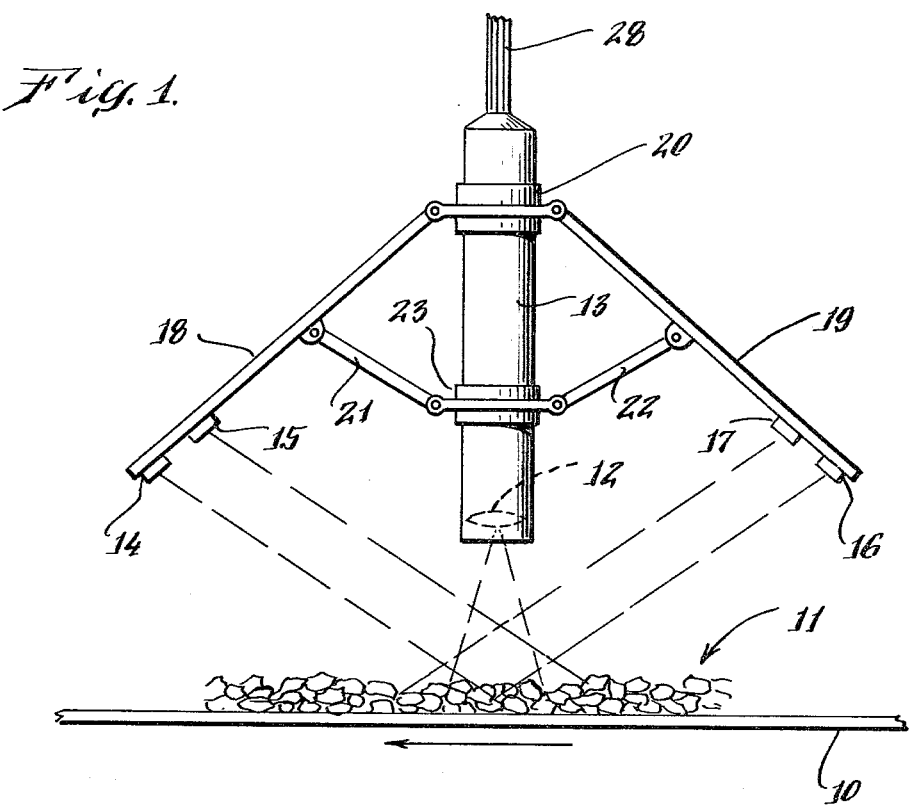
FIG. 1 shows in elevation a light source and transducer assembly in relation to the conveyor.

Referring first to FIG. 1, a conveyor 10 carries mineral particles 11 (moving to the left in the figure) beneath a vertical tubular assembly including an adjustable lens system 12 and a housing 13. A light source comprises two pairs of spaced quartz-iodine lamps 14, 15 and 16, 17 mounted on inclined arms 18 and 19 respectively, pivoted at their upper ends on a collar 20 slidable on the housing 13.

A pair of support arms 21, 22 are pivoted on a further slidable collar 23 on the housing 13, and on intermediate points of the arms 18, 19. The angle of the lamps 14, 15 and 16, 17 and their height above the conveyor 10 can therefore be adjusted, while the intersection of the two beams remains directly below the tubular assembly 12, 13.

The pairs of spaced lamps 14, 15 and 16, 17 ensure that the illuminated space below the assembly extends considerably above the surface of the conveyor 10 and therefore the beams from the lamps illuminate the particles 11 even if well above that surface. The lower edges of the beams, however, cross just above the surface of conveyor 10, so that the unloaded conveyor gives a black field.

Figure 2:
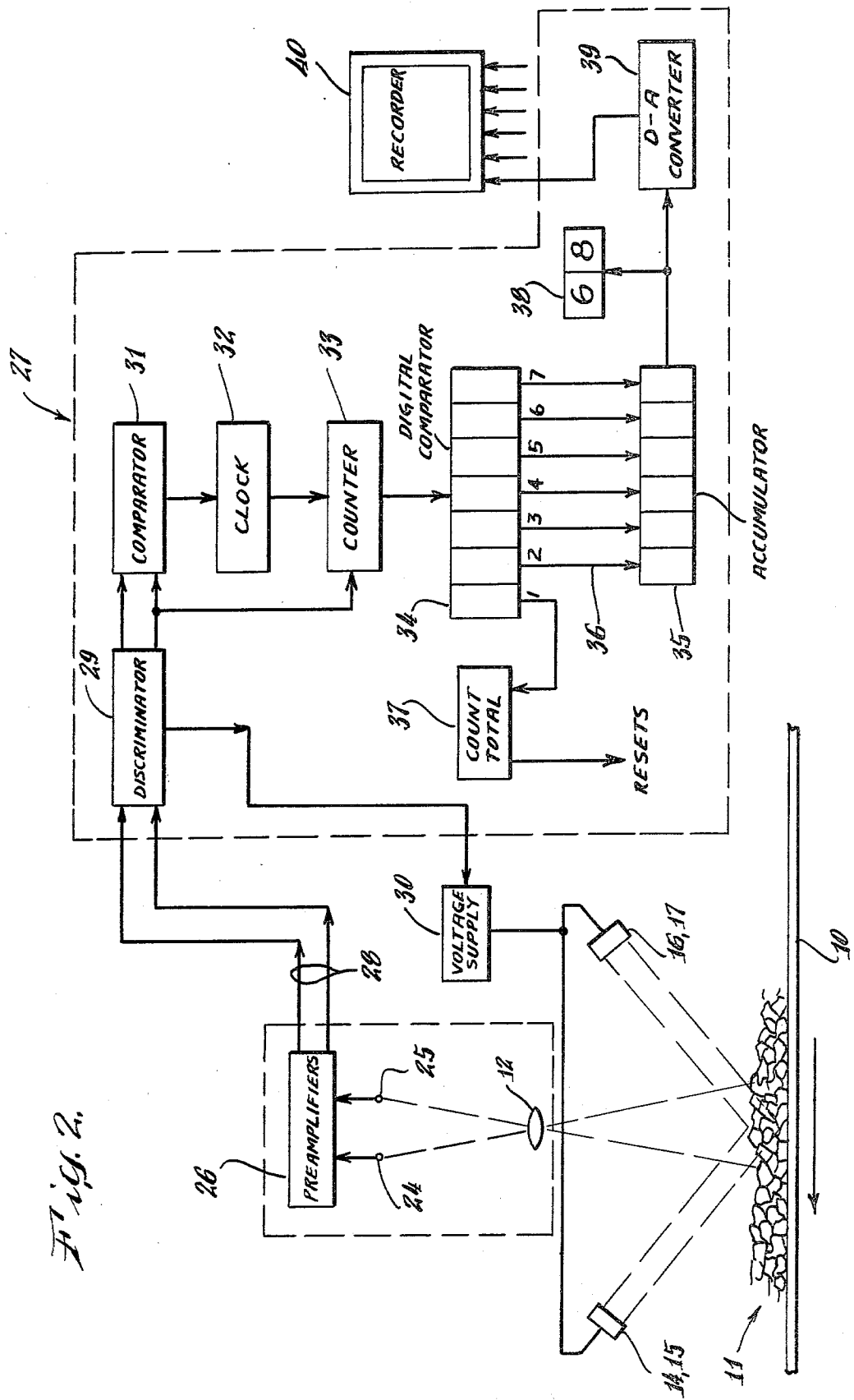
FIG. 2 shows a block diagram of the apparatus generally.

Referring to FIG. 2, an image of the particle field is focussed by the lens 12 upon two photo-transducers or sensors 24, 25 spaced apart in the direction of travel of conveyor 10. In the image cast by the lens 12, the edges of adjacent particles and the boundaries between superimposed or overlapping particles are represented by transmitted light "transitions," illustratively definitive light variations resulting from shadowing produced by the angled light beams. The two transducers 24, 25 produce substantially identical electrical signals corresponding to the light variations of the particle field image, with the signal from the left-hand transducer 24 lagging that of the other transducer 25 by a time inversely proportional to the speed of travel of the conveyor 10.

The two electrical signals from the transducers 24, 25 are separately amplified in preamplifiers 26 and passed to an analyzer and display unit 27 by leads 28 connected to a discriminator 29. This discriminator compares the incoming signals received on lines 28 (a and b in FIG. 3) against a threshold signal level "B," and so generates two corresponding binary "particle-or-gap" signals c and d in which negative-going pulses correspond to dark areas (e.g. gaps) of the image traversed by the transducers 25, 24 respectively. The threshold level is set in accordance with system requirements, and may for example be established as a fraction (typically 40%) of an RC filtered version of the incoming signal a or b. The filter time constant may be related to the mean particle size, for example, the time constant may be of the order of twice the time which a particle of mean particle size takes to move past a fixed point.

The discriminator 29 also may control the light intensity such that the mean amplitude of the incoming signals remains constant. For this purpose, the discriminator may include conventional means to compare input signal amplitude against a set level, and to integrate the resultant difference signal to develop a control signal which is applied to the lamp voltage supply 30 to control its output voltage accordingly. In this way a nonlinear photosensor characteristic of the transducers 24, 25 is prevented from causing a change of signal shape if reflectance of the particle material changes.

Figure 3:
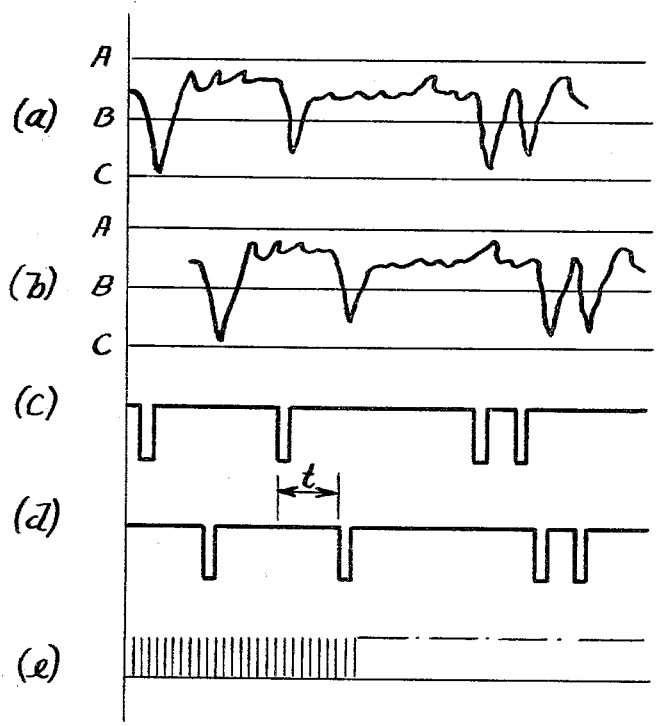
FIG. 3 shows certain of the signals produced in the apparatus of FIG. 2.

A clock pulse generator 32 is provided, and its frequency is controlled in suitable fashion to be inversely proportional to the delay interval between signals c and d ("t" in FIG. 3). In the preferred embodiment, this is accomplished by passing signals c and d from the discriminator 29 to a signal time comparator 31 which controls the frequency of the clock-pulse generator.

In one embodiment, the comparator includes a conventional shift register (not shown) clocked by generator 32, and which serves to delay the leading signal c. The comparator also includes a lead-lag detector circuit which compares the delayed signal c and the lagging signal d to generate a control signal responsive to the time deviation between those signals. This control signal is directed to the clock generator 32 to adjust the clock frequency thereof in a direction to maintain the two signals in coincidence.

The clock pulse sequence is represented at (e) in FIG. 3, and because of the frequency-control described, the interval between pulses represents a constant distance along conveyor 10 irrespective of conveyor speed.

The frequency of the clock pulses is chosen to suit the size distribution of the material and its velocity. As a typical example, this frequency may be 2.4 KHz at a conveyor speed of 1.5 meter/sec. In this case, the distance represented between successive clock-pulses represents 0.625 mm movement of the conveyor belt.

The particle-length data contained in signal c or d can be processed in various ways to determine desired size parameters. For example, in the preferred embodiment one of the signals (d say) is used to gate clock-pulses from the generator 32 to a digital counter 33 when signal d is "high"; the counter then is reset by "high-to-low" transitions of signal d, to terminate the count. The counter 33 therefore produces clock-pulse count outputs each representing the distance travelled by the conveyor 10 between successive shadowed "transitions" scanned by the transducer 24.

The counter 33 is provided with multiple output lines connected respectively to corresponding channels of a seven-channel digital comparator network 34. Each comparator channel output line delivers a pulse when a gated length-count by counter 33 matches a predetermined count preset for the respective comparator channel. These comparator output pulses are counted in seven corresponding BCD accumulators. One accumulator 37 is connected to the comparator channel which is preset to the lowest count and therefore indicates the total number of length counts to be analyzed. The other six accumulators 35 are connected to digital-comparator channels of successively higher preset counts. The number accumulated in a particular accumulator 35 is therefore the number of length counts (from the counter 33) which were larger than or equal to the count preset for that channel.

The accumulated length-count data can be read out in various ways. For example, when the total count of registered length counts in counter 37 reaches a certain number ($10^4$ in the present embodiment), the upper two BCD-digits of each accumulator 35 may be transferred to a corresponding display register 38 and all accumulators reset to zero to begin a new count cycle. While this new count cycle proceeds, the display register holds the fraction of total length counts larger than or equal to the length count preset for each channel, e.g. expressed as per 100 or per 1000 of the total number of length counts dependent on the number of BCD-digits provided in a particular accumulator 35.

The display registers 38 may also be connected to digital-analog converters 39 to provide analog output voltages for each channel, which output voltages in the present embodiment are fed to a multichannel recorder 40.

The apparatus described therefore presents a continuous "on-line" measurement of a number of points on the cumulative frequency distribution of the length intervals between shadowed inter-particle gaps and overlap boundaries along a scan-line in the direction of material movement.

The size distribution of the particles measured and displayed in this form can be transmitted as an input to various manual or automatic control systems of such plant as crushers, screens and pelletisers. Where it is desired to convert the size distribution data in the form described above to an equivalent size distribution in a different form, such as the weight distribution of sieve aperture sizes of the particles, the conversion relationship between the two can be established experimentally and the conversion performed by electronic equipment, such as a computer, which is connected to the apparatus described.

Error in the measurements may be introduced if the material on the belt is "vertically or horizontally segregated" in the sense that the size distribution of the measured surface particles differs from that of a full-depth sample. Material characteristics and belt changing methods largely determine this and the use to which the instrument measurement is to be put influences the degree to which "segregation bias" can be tolerated.

While a single scan line has been described it will be clear that multiple scans spaced across the width of belt 10 may be used.

We claim:

1. A particle size analyzer for use with a moving field of particles comprising an optical assembly producing an image of said moving field by reflected light, said optical assembly including light source means arranged to form a shadow at each edge of adjacent particles and each boundary between superimposed or overlapping particles so as to produce light-intensity transitions at said edge and boundaries; and at least one fixed phototransducer traversed by said moving image producing electrical signals responsive to said light-intensity transitions from which each said edge and boundary is detectable.

2. An analyzer as claimed in claim 1, in which said optical assembly includes a lens mounted with its axis normal to said field, and said light source means includes two directional lights angled oppositely in the direction of movement of said field to illuminate an area of said field on said axis and below said lens.

3. An analyzer as claimed in claim 2, in which the angle of said lights and their height above said field are adjustable.

4. An analyzer as claimed in claim 10, in which said signal processing means includes a discriminator fed by said electrical signal and producing a pulse signal for each said edge and boundary.

5. An analyzer as claimed in claim 4, in which said signal processing means includes a clock-pulse generator; a counter for clock-pulses; and connections for enabling and resetting said counter by successive ones of said pulse signals.

6. An analyzer as claimed in claim 5 including two photo-transducers spaced in the direction of movement of said field to give similar leading and lagging electrical signals; said analyzer means comprising a comparator responsive to the time-delay between said leading and lagging signals; and means controlled by the output of said comparator to vary the frequency of said clock-pulse generator in inverse proportion to said time interval, whereby the interval between successive clock-pulses represents a constant distance of movement of said field irrespective of its speed of movement.

7. An analyzer as claimed in claim 6, in which said signal processing means includes a multi-channel digital comparator giving an output for each channel when the count in said counter reaches a count preset for that channel.

8. An analyzer as claimed in claim 7, including a plurality of accumulators each fed from an output of said digital comparator, each accumulator containing the number of said length counts of not less than said preset count; and means responsive to a predetermined count in that accumulator which is preset to the lowest count to reset said accumulators to begin a further cycle of said counts.

9. An analyzer as claimed in claim 8, in which said output means includes a means to display the signal from each said accumulator.

10. An analyzer as claimed in claim 1, including signal processing means fed by said electrical signals to derive size parameters of said particles from the spacing of said edges and boundaries.

11. The method of analyzing the sizes of particles being transported along a path by means of a conveyor belt or the like, wherein the particles are closely packed such as to be to a considerable extent superimposed and/or overlapping; said method comprising the steps of:
   directing at least one beam of light towards a region traversed by said moving particles, said beam striking said region at a predetermined angle with respect to the direction of movement of said particles to produce in said region shadows defining edges of particles and/or boundaries between superimposed or overlapping particles;
   sensing the intensity of light reflected from said particles in said region resulting from said beam of light directed thereto, the detection of said reflected light being effected at an angle different from said predetermined angle such that the intensity of the reflected light will be responsive to the occurrence of said shadows in said region; and
   detecting when said reflected light intensity falls below a preselected level indicating the appearance of said shadows in said region;
   whereby the detection of said shadows may be used to produce signals to be processed for determining the sizes of said particles.

12. The method of claim 11, wherein two beams of light are directed towards said region from opposite sides thereof to intersect adjacent said region;
   the sensing of said reflected light being effected from a position between said two light beams, above the intersection thereof.

13. The method of claim 12, wherein the vertical projections of both of said beams on said moving particles are parallel to the direction of movement of said particles.

14. The method of claim 12, wherein said intersection of said beams occurs above the upper surface of said particles.

15. The method of claim 14, wherein the particles are carried by a conveyor, and wherein two additional beams of light are angled from opposite sides of said region to intersect below the upper surfaces of said particles but above the surface of said conveyor, whereby the unloaded conveyor gives a black field.

16. An analyzer for determining the sizes of particles located within a field of particles comprising:
   an optical assembly including light source means for producing an image of said particle field by reflected light;
   at least one photo-transducer for sensing the intensity of light reflected from said particle field image;
   means for producing relative motion between said particle field image and said photo-transducer such that said photo-transducer effectively traverses said image along a predetermined line of view;
   said light source means being arranged at a predetermined angle such that shadows are created, and appear in said image, as a result of light rays passing by particle boundaries disposed along said line of view;
   said photo-transducer producing electrical signals responsive to said shadows from which said particle boundaries are detectable along said line of view; and
   signal processing means responsive to said electrical signals operable to derive size parameters respecting said particles.

17. An analyzer as claimed in claim 16, wherein said photo-transducer is arranged to sense reflected light arriving on a path having an angle different from said predetermined angle.

18. The method of analyzing the sizes of particles located within a field of particles comprising the steps of:
   directing at least one beam of light towards a region of said particle field, said beam striking said region at a predetermined angle to produce in said region shadows corresponding to particle boundaries;
   sensing along a predetermined line of view the intensity of light reflected from said particle field resulting from said beam of light directed thereto, such that said intensity of the sensed reflected light will be responsive to the occurrence of said shadows along said line of view;
   detecting when said reflected light intensity indicates the appearance of said shadows along said predetermined line of view;
   producing signals responsive to the detection of said shadows; and
   processing said signals to determine the sizes of said particles.

19. The method of claim 18, wherein said sensing is effected by a photo-transducer; and
   providing relative motion between said particle field and said photo-transducer to effect sensing of said intensity of light along said predetermined line of view.

20. The method of claim 18, wherein said reflected light is sensed at an angle different from said predetermined angle.

* * * * *